United States Patent [19]

Park et al.

[11] Patent Number: 5,171,881
[45] Date of Patent: Dec. 15, 1992

[54] PROCESS FOR PRODUCING TRIMELLITIC ACID

[75] Inventors: Sang H. Park; Jae S. Go; Jung W. Sim, all of Ulsan; Chun G. Kim, Seoul, all of Rep. of Korea

[73] Assignee: Yukong Limited

[21] Appl. No.: 619,553

[22] Filed: Nov. 29, 1990

[30] Foreign Application Priority Data

Apr. 3, 1990 [KR] Rep. of Korea .............. 4578

[51] Int. Cl.$^5$ ......................... C07C 51/265
[52] U.S. Cl. ..................... 562/413; 562/416; 562/417
[58] Field of Search ........................ 562/413

[56] References Cited

U.S. PATENT DOCUMENTS 4,835,308  5/1989  Sakakibara et al. ................ 562/413

FOREIGN PATENT DOCUMENTS 57-128730  8/1982  Japan .
57-167942  10/1982  Japan .
58-39813  3/1983  Japan .

Primary Examiner—Jose G. Dees
Assistant Examiner—Vera C. Clarke
Attorney, Agent, or Firm—Lowe, Price, LeBlanc & Becker

[57] ABSTRACT

It is a process for producing trimellitic acid (trimellitic acid, 1, 2, 4-tricarboxylic acid) by oxidizing pseudocumene with a molecular oxygen containing gas. More particularly, pseudocumene is oxidized into trimellitic acid by introducing a molecular oxygen containing gas in an acetic acid solvent in the presence of oxidizing catalysts, wherein the oxidization reactions in two different stages which have different ranges of temperature and different compositions of catalyst, respectively.

9 Claims, No Drawings

PROCESS FOR PRODUCING TRIMELLITIC ACID

BACKGROUND OF THE INVENTION

1. Field of the Invention

The present invention relates to a process for producing trimellitic acid, which enables to be suitably used as a raw material in the fields of thermostable plasticizers and various heat-resistant polymers, by the oxidization of pseudocumene with a molecular oxygen containing gas in an acetic acid solvent in the presence of catalysts.

2. Description of the Prior Art

Trimellitic acid is a very useful raw material for thermostable plasticizers or various heat-resistant polymers (Thermoplastics), so it has been demanded to develop an economical and effective process which enables to obtain a pure trimellitic acid.

Various processes have been introduced previously, which produce trimellitic acid by oxidizing pseudocumene with a molecular oxygen containing gas in an acetic solvent in the presence of a catalyst comprising heavy metal compounds and one or more bromine compounds. The methods characterized by continuously conducting the oxidization are described in for instance, Japanese Patent Laid-open No. 57-128730, Japanese Patent Publication No. 58-39813, Japanese Patent Laid-open No. 57-167942, and U.S. Pat. No. 4,835,308.

However, each of the above methods is still not properly applicable in the practical use even though each method is advantageous to obtain a relatively good quality product continuously.

The method described in Japanese Patent Publication No. 58-39813 is not only a complicated process characterized by conducting the oxidization with multi-stage operations by changing the composition of the quarternary catalyst comprising cobalt, manganese, cerium and bromine from one stage to another, but also an uneconomical process because the recycling of the catalyst which is very expensive is practically impossible due to the necessity that the composition of the catalyst has to be adjusted in each stage.

The method described in Japanese Patent Laid-open No. 57-128730 is a multi-stage oxidization process characterized in that the reaction in the first stage of the batchwise manner is conducted by introducing a series of catalysts such as cobalt, manganese and bromine, in a state of relatively low temperature range (110° C. -170° C.) until the more than 2.8 mole oxygen per mole of pseudocumene is consumed and the oxidization is then completed in the second stage of the reaction which is a continuously-flow oxidization process with a constant high temperature. In said process, the reaction in the first stage is to start at constant temperature (example 1:110° C.) and the temperature is to increase as the consumption rate of oxygen is gradually decreasing after passing through critical maximum value. The reaction is to be completed by means of supplying more than 2.8 mole oxygen per mole of pseudocumene after suspending elevating a temperature at the temperature (example 1:150° C.) when oxygen is moderately actively consumed again.

This method, however, has disadvantages that the yield of and the selectivity for trimellitic acid are not sufficiently high since the oxidization of pseudocumene to carbon dioxide and water, which is the most undesired side reaction for the selective oxidization of pseudocumene to trimellitic acid occurs, and that the operational difficulty carefully to convert and control temperature in the first stage is severe.

The method described in Japanese Patent Laid-open No. 57-167942 is a continuous oxidization process, composed of two stage reactions that require two sets of consecutive reactors at each stage, is characterized in that the oxidization at the first stage of reaction is successively conducted by introducing cobalt, bromine and a little portion of manganese into the first reactor and the outflow from the first reactor is reacted again in the second reactor under the same condition as the first reactor until the concentration of the unreacted pseudocumene is less than 0.4% by weight. Thereafter, at the second stage of reaction, the rest of manganese thereof is added in the third reactor to oxidize the outflow from the second reactor and then the oxidization is completed in the fourth reactor.

However, this method is designed actually for improving the effectiveness of the second stage oxidization by the addition of manganese, but thereby the composition of the catalyst used in the first stage oxidization is not suitable and therefore the oxidization of pseudocumene to carbon dioxide and water, which is the most undesired side reaction for the selective oxidization of pseudocumene to trimellitic acid, is relatively remarkable. In addition, as the reaction proceeds, an increase of the amount of trimellitic acid may cause auto-controlling effect which diminish the reaction rate instead of auto-oxidization which increase it.

Therefore, the method described in Japanese Patent Laid-open No. 57-167942 has a series of disadvantages as follow: (a) the yield of and the selectivity for trimellitic acid are not sufficiently high, (b) the operation is complicated, and (c) the recycling of the used catalyst is practically difficult.

The method described in the U.S. Pat. No. 4,835,308 also relates to the two stage oxidization process characterized in that the first stage oxidization is conducted at 110° C. -180° C. by introducing the whole quantity of catalysts and the second stage oxidization at 180° C. -230° C. without any catalyst.

The above-mentioned method enables to solve the difficulty of the recycling of the used catalyst but the concentration of the pseudocumene in the initial oxidization is so extremely high that it can not control the rate of oxidization properly. Furthermore, it can provide an insufficient yield and an unsatisfactory purity of trimellitic acid because a low concentration of the dissolved oxygen in the solution cause to promote a radical dimerization reaction which enables to produce a byproduct having a high boiling temperature.

Furthermore, as the reaction proceeds, the concentration of trimellitic acid increases. The increase thereof cause the formation of insoluble precipitations together with metallic catalyst, and as a result, it may considerably effect the contamination of trimellitic acid and decrease the yield of trimellitic acid.

SUMMARY OF THE INVENTION

The present invention is designed for improving the difficulties found in the above prior arts and providing an excellent and feasible process to be applicable directly to the industry that demands trimellitic acid, which need a simplicity of operation since a radical dimerization reaction that produce by-products having a high boiling temperature and a the complete oxidization that produces carbon dioxide and water can be restricted, and a remarkable enhancement in the yield of trimellitic acid as well due to the highly activated catalyst, by the oxidization of pseudocumene with a gas containing molecular oxygen, preferably air.

As this result of our extensive study to overcome disadvantages of the said patents, we have found that the object of the present invention can be easily achieved by employing at least two reaction-stages having different reaction temperatures wherein the initial oxidization is made by introducing a part of the specific catalyst-components into the first stage of the reaction and then the oxidization at the second stage of the reaction is completed by introducing the rest of the catalyst components in a state of an aqueous solution.

The present invention provides a process for producing trimellitic acid by oxidizing pseudocumene with a molecular oxygen containing gas in an acetic acid solvent in the presence of a catalyst comprising cobalt, manganese and bromine, wherein the oxidization is initiated and conducted by introducing the whole predetermined amounts of the cobalt, bromine and acetic acid solvent into the first stage of the reaction and employing some amounts of oxygen in the range of 2.5 to 3.3 mole, preferably 2.6 to 2.9 mole, based on 1 mole of pseudocumene.

The oxygen of above-mentioned range can oxidize selectively on one or two methyl groups of benzene ring to prevent a catalyst from being poisoned and dilute the concentration of pseudocumene to prevent a by-product from being produced due to the radical dimerization reaction.

At the second stage of the reaction, the aqueous manganese solution is introduced to further oxidize an intermediate which is already oxidized to one or two methyl group of benzene ring to complete the oxidization when trimellitic acid is generated.

Additionally, the manganese compound in state of aqueous solution (15 to 25 wt %) is introduced to make a dilution of high concentration of trimellitic acid formed as the oxidization proceeds and it prevents the insoluable precipitation due to the reaction of the cobalt metal and manganese metal with trimellitic acid and the deactivation of catalysts.

DETAILED DESCRIPTION OF THE INVENTION

The present invention concerns on a process for producing trimellitic acid and its production procedure is described below in more detail.

At the first reaction stage, a pseudocumene is oxidized initially with a molecular oxygen containing gas in an acetic acid in the presence of the oxidization catalysts with maintaining a temperature in the range of 110° to 170° C. wherein the cobalt compound as a catalyst is about 0.01 to 1.0 wt % of the acetic acid solvent based on cobalt metal, and the weight ratio of bromine compound to cobalt metal (Br/Co) is in the range of 0.5 to 10.

After then, at the second reaction stage, the manganese compound in an aqueous solution state is introduced into a reactor with a molecular oxygen containing gas as an oxidizing agent in the condition of maintaining a temperature in the range of 180° to 220° C. and then reaction is substantially completed.

The oxidization reaction at the first stage is preferably continued until the conversion rate of pseudocumene in the first reaction stage reaches more than 90% and the amount of acetic acid as a solvent is more than double by weight, preferably from 4 to 12 times, based on the weight of pseudocumene and it may be acceptable as far as a water in concentration of acetic acid is not more than 5 to 30% by weight.

The oxidizing catalyst systems are composed of cobalt compound, manganese compound, and bromine compound and those specifications are as follows; cobalt compound and manganese compound can be used if they are soluble in acetic acid, and suitable forms of cobalt and manganese can be, for example, the salts of organic acids such as acetates, propionates, naphthenates, octenates and the likes thereof, hydroxides, halides such as chlorides, bromides and the likes thereof, the salts of inorganic acids such as borates, nitrates, carbonates and the likes thereof. The more preferable forms of cobalt and manganese are the acetate, bromides or phosphates and acetates is the most desirable.

The bromine compounds which can be feasibly used, are bromine, hydrogen bromide, ammonium bromide, alkali metal bromides such as sodium bromide, lithium bromide and potassium bromide, inorganic bromides such as cobalt bromide and manganese bromide and organic bromides such as tetrabromoethane, acetylbromide, benzyl bromide and the likes thereof. Among these compounds the more preferable compounds are sodium bromide, cobalt bromide, manganese bromide or ammonium bromide, and the most desirable compound is sodium bromide. In particular, each of cobalt compounds, manganese compounds, and bromine compounds as described above can be used alone or combined compounds comprising two more components.

The total amount of the cobalt compound has to be kept in the range of 0.01 to 1.0% by weight of the acetic acid solvent based on cobalt metal.

When the cobalt catalyst is used in an amount of less than 0.01 wt % based on the above cobalt metal, the reaction rate will be significantly decreased, and on the other hand. When it is used in an amount of more than 1.0 wt % based on the above cobalt metal, a yield of and a selectivity for the trimellitic acid as a final product will be decreased since the side reaction which produce carbon dioxide and water by oxidizing pseudocumene occurs and by-products having a high boiling temperature and insoluble complexes are produced.

The total amount of manganese compound based on the atomic ratio of manganese to cobalt (Mn/Co) is desirable in the range of 0.1 to 0.7, more preferably 0.2 to 0.5, and these have a good activity, selectivity and recovery of the catalysts.

In the second stage of the reaction, the added aqueous solution of manganese compound is desirable in the range of 15 to 25% by weight based on acetic acid. The atomic ratio of the total amount of the bromine compound to that of cobalt metal in the cobalt compound (Br/Co) is in the range of 0.5 to 10 and preferably no less than 1.0. When the total amount of the bromine catalyst is used in an amount of less than 0.5 by the atomic weight ratio, the activity of the catalyst will not be sufficiently high.

On the other hand, if the ratio is more than 10, the concentration of bromine-components in the final product will be unnegligible even though the catalytic activity normally increase, and therefore it results in increasing the cost of the catalyst and the cost for purification of the product and decreasing the efficiency of recovering the catalysts.

A preferred process according to the invention as described above is a process wherein the atomic ratio of bromine to cobalt and manganese (Br/(Co+Mn)) is in the range of 0.5-2.0.

That is to say, this invention is characterized in that in oxidizing a pseudocumene into a trimellitic acid, total amount of the cobalt compound and the bromine compound dissolved in acetic acid solvent are introduced into the first stage of the reaction, the manganese compound dissolved in a water in state of an aqueous solution is inserted into the second stage of the reaction, and the oxidization reactions in above each stage are made by adding the gas containing molecular oxygen as an oxidizer and maintaining the each stage in specific range of temperature, respectively.

A purified oxygen or air can be used for a suitable molecular oxygen containing gas as the oxidizing agent, but the air can be normally used for industry. The molecular oxygen containing gas is usually supplied continuously into the liquid reactant mixture through one or more gas inlets of the reactor and, in case that the reaction is conducted by multi-stage reactors, the molecular oxygen containing gas is continuously introduced by controlling its feed rate into each reactor through one or more gas inlets of each reactor.

The reaction temperatures in the first and second stage have to be maintained in the range of 110° to 170° C. and 180° to 220° C., respectively. If the reaction temperature at the first stage is lower than 110° C., the reaction rate may extremely be low; and if it is higher than 170° C., undesired side reactions such as the complete oxidization will increase, the dealkylation of pseudocumene due to the pyrolysis may produce phthalic acid, and moreover, the deactivation of the catalyst may occur.

On the other hand, if the reaction temperature at the second stage is lower than 180° C., it is difficult to complete an oxidization into a trimellitic acid; and if it is higher than 220° C., the decompositions of solvents and reactants into carbon dioxide will increase, and simultaneously the colored impurities increase.

The reaction pressure has to be maintained in the range in which the acetic acid solvent can be kept to be a liquid phase at the reaction temperature employed, preferably in the range of 250 to 450 psig. With respect to the partial pressure of the oxygen over the reaction system, it is preferable to control the flow rate of the molecular oxygen containing gas into the reactor to keep the concentration of oxygen in the off-gas out of the reactor to be in the range of 1 to 8% by volume.

The oxidization of the present invention, may be completed by conducting the reaction of the second stage after the reaction of the first stage and may be obtainable in the batch operation or the continuous flow method, which enables to be conducted by multi-stage of reaction.

As a result, the present invention according to the above process shows that the yield of trimellitic acid can be obtainable up to 95.4 mole % and the purification of the products can be very easy after the reaction.

While the invention has been particularly described above with respect to specific procedures, it will be recognized that those procedures are presented for purposes of illustration only and not intended to be limited.

The present invention is illustrated in more details by the following examples. However, these examples are not to be construed to limit the scope of the invention.

EXAMPLE 1

A one (1) gallon autoclave reactor made from titanium equipped with a reflux condenser, a stirrer, and a nozzle for air-blowing was used for reactions. 80.53 g of pseudocumene, 2.704 g of cobalt acetate, 1.127 g of sodium bromide and 640 g of acetic acid as a solvent were charged into the reactor. The reactor was purged by a helium as an inert gas before reaction thereof, and the temperature thereof was elevated to 140° C. The reaction was initiated by introducing a compressed air into the autoclave reactor with constant 350 psig pressure. The injection of the compressed air was suspended after 90 minute from the initial reaction time and 1.429 g of manganese acetate dissolved in 125 g of water was introduced into the reactor with elevating temperature up to 205° C.

The oxidization reaction was continuously carried out by introducing the compressed air into the reactor again. The concentration of oxygen in the off-gas was analyzed by the gas chromatography.

The compressed air injection was suspended and the reaction was terminated when the concentration of oxygen in the off-gas was just over 8 volume %. After the reaction was completed, the reaction products were taken out from the reactor, and the reaction products were converted to the corresponding methyl esters by esterification, and then the resulting esters were quantitatively analyzed by the gas chromatography. As a result of the above procedure, a yield of trimellitic acid was 95.4 mole %, a selectivity for methyl phthalic acid, phthalide, and trimellitic acid were 1.5 wt %, 0.6 wt %, and 96.5 wt %, respectively. A series of EXAMPLES from EXAMPLE 2 to 5, which were carried out with same procedure as EXAMPLE 1, were presented in TABLE 1 in detail. A phthalide herein was a 4-carboxy-1:2-phthalide or namely 5-carboxyphthalide.

COMPARATIVE EXAMPLE 1.

Under the same procedure as EXAMPLE 1 above, the first stage of the reaction was carried out at 140° C. for 90 minutes by introducing 620 g of acetic acid, 80.9 g of pseudocumene, 2.619 g of cobalt acetate and 7.18 g of sodium bromide, and the second stage of the reaction was made by introducing 1.382 g of manganese acetate dissolved in 80 g of acetic acid until the reaction temperature was elevated up to 205° C.

As a result, a selectivity for methylphthalic acid, phthalide, and trimellitic acid were 4.8 wt %, 3.0 wt %, and 90.4 wt %, respectively, and a yield of trimellitic acid was 88.9 mole %.

COMPARATIVE EXAMPLE 2.

The reaction was carried out at 205° C. for 150 minutes by introducing 640 g acetic acid, 80.55 g of pseudocumene, 2.72 g of cobalt acetate, 1.43 g of manganese acetate, and 7.42 g of sodium bromide in the same reactor as EXAMPLE 1 using the same method as EXAMPLE 1.

As a result, a selectivity for methylphthalic acid, phthalide, and trimellitic acid were 7.2 wt %, 5.7 wt %, and 86.2 wt %, respectively, and a yield of trimellitic acid was 84.9 mole %.

TABLE 1

| REACTANTS AND REACTION CONDITION | UNIT | EX. 2 | EX. 3 | EX. 4 | EX. 5 |
|---|---|---|---|---|---|
| Pseudocumene | g | 80.53 | 80.28 | 80.27 | 80.11 |
| Cobalt Acetate | g | 2.617 | 1.623 | 1.083 | 2.702 |
| Cobalt/Acetic Acid | wt % | 0.1 | 0.06 | 0.04 | 0.1 |
| Manganese Acetate (1) | g | 0 | 0 | 0 | 0 |
| manganese/Cobalt | wt % | 0 | 0 | 0 | 0 |
| Manganese Acetate (2) | g | 1.382 | 0.856 | 0.572 | 0.713 |
| Manganese/Cobalt | wt % | 0.5 | 0.5 | 0.5 | 0.25 |
| Sodium bromide | g | 7.18 | 4.45 | 1.484 | 7.424 |
| Bromine/Cobalt | wt % | 9 | 9 | 4.5 | 9 |
| Acetic acid | g | 640 | 640 | 640 | 640 |
| Reactor Pressure | psig | 350 | 350 | 350 | 350 |
| Reaction Temp. (1) | C | 140 | 140 | 140 | 140 |
| Reaction Temp. (2) | C | 205 | 205 | 205 | 205 |
| Air Rate | Nl/10 min | 24.32 | 24.32 | 24.32 | 24.32 |
| Reaction Time (1) | min. | 90 | 90 | 90 | 90 |
| Reaction Time (2) | min. | 70 | 70 | 70 | 70 |
| R.P.M. | | 500 | 500 | 500 | 500 |
| Water | g | 125 | 125 | 125 | 125 |
| Dimethylbenzene carboxylic acid | wt % | 0 | 0 | 0 | 0 |
| Methylphthalic acid | wt % | 2.3 | 3.2 | 4.81 | 1.4 |
| Phthalide | wt % | 1.6 | 2.5 | 1.57 | 1.4 |
| Trimellitic acid | wt % | 95.4 | 93.3 | 93.1 | 96.3 |
| Yield of Trimellitic acid | mole % | 89.7 | 89.6 | 92.1 | 93.3 |

Remark:
(1): first stage
(2): second stage

What is claimed:

1. A process for producing trimellitic acid by the liquid phase oxidation of pseudocumene with a molecular oxygen containing gas in an acetic acid solvent in the presence of an oxidation catalyst comprising cobalt compounds, manganese compounds, and bromine compounds: wherein the reaction pressure is maintained in the range of 250 to 450 psig, the total amount of cobalt compound based on the weight of cobalt metal is in the range of 0.01 to 1.0% by weight of the acetic acid solvent, the total amount of manganese compound based on the atomic ratio of manganese to cobalt is in the range of 0.1 to 0.7, and the total amount of bromine compound based on the atomic ratio of bromine to cobalt is in the range of 0.5 to 10;

and wherein the process comprises at least two reaction stages wherein at the first stage the reaction temperature is maintained in the range of 110° to 170° C., and at the second stage the succeeding temperature is maintained in the range of 180° to 220° C.;

wherein at the first reaction stage the entire amounts of the cobalt compound, bromine compound, acetic acid solvent, and the reactants except the manganese compound are introduced;

wherein at the first reaction stage the oxidation reaction proceeds by providing oxygen in the range of 2.5 to 3.3 mole on the basis of 1 mole pseudocumene until the conversion of pseudocumene becomes more than 90%;

and wherein at the second stage the reaction is virtually completed by providing the manganese compound in water solution in which the amount of water is added together with 5 to 30% by weight of acetic acid.

2. A process according to claim 1, wherein the cobalt compound is cobalt acetate.

3. A process according to claim 1, wherein the manganese compound is manganese acetate.

4. A process according to claim 1, wherein the bromine compound is sodium bromide.

5. A process according to claim 1, wherein the cobalt compound is cobalt acetate, the bromine compound is sodium bromide, and the manganese compound is manganese acetate.

6. A process according to claim 1, wherein the weight ratio of acetic acid to pseudocumene is 4 to 12.

7. A process according to claim 1, wherein the weight ratio of bromine to cobalt and manganese is in the range of 0.5 to 2.0.

8. A process according to claim 1, wherein the oxidation reaction in the first stage is to provide 2.6 to 2.9 mole oxygen on the basis of 1 mole pseudocumene until the conversion of pseudocumene becomes more than 90%.

9. A process according to claim 1, wherein the molecular oxygen containing gas is air.

* * * * *